(12) United States Patent
Andersen

(10) Patent No.: US 7,593,534 B2
(45) Date of Patent: Sep. 22, 2009

(54) TRANSDUCER FOR BIOACOUSTIC SIGNALS

(75) Inventor: Bjoern Knud Andersen, Struer (DK)

(73) Assignee: Bang & Olufsen Medicom A/S, Struer (DK)

( * ) Notice: Subject to any disclaimer, the term of this patent is extended or adjusted under 35 U.S.C. 154(b) by 858 days.

(21) Appl. No.: 10/518,588

(22) PCT Filed: Jun. 23, 2003

(86) PCT No.: PCT/DK03/00427

§ 371 (c)(1),
(2), (4) Date: Dec. 21, 2004

(87) PCT Pub. No.: WO04/002191

PCT Pub. Date: Dec. 31, 2003

(65) Prior Publication Data

US 2005/0232434 A1    Oct. 20, 2005

(51) Int. Cl.
*A61B 7/04* (2006.01)
(52) U.S. Cl. .......................... 381/67; 181/131; 181/132
(58) Field of Classification Search .................. 381/67; 181/171–172, 131–132
See application file for complete search history.

(56) References Cited

U.S. PATENT DOCUMENTS

| 5,467,775 | A | | 11/1995 | Callahan et al. | |
|---|---|---|---|---|---|
| 5,492,129 | A | * | 2/1996 | Greenberger | 600/528 |
| 5,610,987 | A | | 3/1997 | Harley | |
| 5,883,339 | A | * | 3/1999 | Greenberger | 181/131 |
| 5,909,495 | A | | 6/1999 | Andrea | |
| 6,028,942 | A | | 2/2000 | Greenberger | |
| 6,160,897 | A | * | 12/2000 | Klein | 381/396 |
| 6,912,287 | B1 | * | 6/2005 | Fukumoto et al. | 381/151 |
| 6,925,191 | B2 | * | 8/2005 | Petroff et al. | 381/423 |

* cited by examiner

*Primary Examiner*—Vivian Chin
*Assistant Examiner*—Disler Paul
(74) *Attorney, Agent, or Firm*—David S. Safran; Roberts Mlotkowski Safran & Cole, P.C.

(57) ABSTRACT

In well-known electronic stethoscopic transducers the sensitive element is influenced by signals transmitted via the skin, and the rear side is enclosed in a housing to prevent airborne noise from reaching the sensitive element. According to the invention, an improved signal-to-noise ratio is obtained by letting the transducer be a piezoelectric transflexural diaphragm in contact with the skin, the rear side of the diaphragm communicating with the surrounding air via an acoustical network, thereby receiving airborne noise which acts to counteract the influence of noise coming from the skin.

12 Claims, 7 Drawing Sheets

TRANSDUCER FOR BIOACOUSTIC SIGNALS

BACKGROUND OF THE INVENTION

1. Field of Invention

The invention concerns a transducer for bioacoustic signals comprising a transducer element having a front side and a rear side, the front side of which may establish an intimate contact with the surface of a body part, said surface being the transmitter of direct interior sound from the body, said transducer element being mounted in a housing subject to airborne noise, and having a surface surrounding the front side of said transducing element, said element and said surrounding surface being in intimate contact with the surface of said body part during use.

2. Description of Related Art

Transducers for bioacoustic signals emanating from a body usually belong to two main types applied to an outside surface of the body. One type is a microphone in principle, in which the vibration of a delimited area of skin is picked up as pressure variations in the air surrounding the area of skin, usually the pressure variations in a closed volume delimited by the skin, the microphone diaphragm, and the housing. An enclosed volume is essential to obtain a good low frequency response as well as protection from extraneous airborne noise—one early example is the standard binaural stethoscope in which the bell defines the volume. The second type is an accelerometer in principle, in which a light-weight housing rests against the part of the body and the inertial mass inside provides reference in the generation of signals proportional to the instant acceleration. This type has in itself a good protection against extraneous airborne noises, but the sensitivity decreases and the electrical noise increases very much in the lower end of the frequency range of interest, unless the inertial mass is increased to a value in which it unavoidably influences the actual measurement. There is hence a need for an improved transducer.

It has been determined that extraneous airborne noise in general enters the transducer mainly by two routes. One is direct airborne influence on the transducing element itself, e.g., a microphone diaphragm. The other is by means of influence on the diaphragm from the skin in touch with the diaphragm, while the housing is receiving airborne noise. A further contribution may be airborne noise radiated into the body around the housing surrounding the transducer in contact with the body, said airborne noise being converted to pressure waves which are re-radiated from the part of the skin directly in touch with the diaphragm. This type of noise injection is not avoided by enclosing the area of skin, however the phase relations to the desired signal are such that the contribution would generally be of minor importance. There is hence a further need to address in an improved construction of a transducer for bioacoustic signals.

In U.S. Pat. No. 5,610,987 a solution is given, which utilises a piezoelectric transflexural diaphragm in direct contact with the skin in the area within the surrounding housing. In this case, the noise signal is coupled to the diaphragm without re-radiation, and the rear of the diaphragm is shielded against extraneous noises by the housing. In order to obtain noise cancellation, this patent also describes that the housing contains an identical but outwards-facing piezoelectric transflexural diaphragm which is only subjected to airborne noise, and that a further identical transducer is placed in contact with the body some distance from the first transducer. Extensive digital signal processing enables a high degree of elimination of the undesired noises. This makes the equipment expensive and causes a need for re-programming if the sensor part is exchanged.

U.S. Pat. No. 6,028,942 relates to the chestpiece of an acoustic, non-amplified stethoscope having noise balancing means, in that a resonator is coupled to the reverse side of the diaphragm. An embodiment using amplification is also shown. The purpose is to compensate the noise that is radiated into the tissue surrounding the front end when applied to the skin and which is added to the desired signal. There is an air space between the tissue and the diaphragm that provides the output signal, however this remarkably reduces the usefulness of the device in practice. It is probable that the elaborate equivalent circuits used in U.S. Pat. No. 6,028,942 are misleading, because they do not take into account the pickup of airborne noise via the transducer housing mass itself.

SUMMARY OF THE INVENTION

The invention is based on a recognition that there is indeed a significant pickup of airborne noise by the housing of the transducer, and that the ensuing vibration of the housing acts on the diaphragm by pressing against the outer surface of the body. If the reverse side of the diaphragm picks up the extraneous airborne noise in a suitable phase relationship, the influence of the airborne noise, will be effectively eliminated in a frequency interval of interest. The proper phase relationship may be available in a very narrow frequency range by just providing access for airborne noise to the rear side of the diaphragm, but further improvement in a frequency interval of interest may be obtained by suitable acoustical loading of the rear side of the diaphragm. In particular, it has been demonstrated that an important improvement is obtained by reducing that proportion of the surface of the transducer presented to the outer surface of the body that is constituted by the diaphragm. Hence, the invention is in particular that the effective area of the transducing element is less than 50% of the area of the surrounding surface of the housing and in that the rear side of the transducing element is loaded by an acoustical network which is in communication with the surrounding air, said loading creating an extinguishing relationship between airborne noise signals influencing the front and rear sides of the transducing element respectively. The invention takes account of the fact that there are several paths of both the desired physiological signals and the offending airborne noises, and that influencing the housing also causes an influence on the transducing element.

An advantageous embodiment of the invention is in particular that the effective area of the transducing element is between ½ and ¹⁄₁₀₀₀ of the area of the surrounding surface of the housing. It has been determined that there is an improvement in performance when the respective areas are held within these proportions. The effect may be related to the area of contact to the skin and the density of the underlying tissue. By effective area is meant the area of the diaphragm that is actually flexing and contributing to the output, i.e. it is usually less than the opening in the surrounding surface.

In a further advantageous modification this ratio is within the interval $0.2 \geq ad/ah \geq 0.05$.

An advantageous embodiment is in particular that the transducing element is a compound diaphragm giving an electrical output when exposed to bending. This may be obtained in the form of what has been termed a piezoelectric transflexural diaphragm, which is in fact a very thin piezoelectric layer, one side of which is usually bonded to a metal diaphragm and which has a metal layer deposited on the other side. This laminate reacts to shear stresses in the piezoelectric layer occurring when the diaphragm is bent inwards and outwards by generating a voltage difference between the metal diaphragm and the metal deposit.

A further advantageous embodiment is in particular that the transducing element is a compound diaphragm giving an electrical output when exposed to differential stretching of the front side with respect to the rear side of the diaphragm. This is slightly different construction, which may give advantages for particular ad/ah ratios.

A further advantageous embodiment is in particular that the acoustical network consists of a cavity in the housing being indirectly influenced by airborne noise.

A further advantageous embodiment is in particular that the acoustical network consists of a cavity and at least one port in the housing. This is in fact an enclosure for the diaphragm with a leak, and by suitably placing the resonant frequency of this cavity volume and port combination, an extension of the frequency response and in particular of the range of noise suppression may be obtained.

A further advantageous embodiment is in particular that the acoustical network consists of a cylindrical conduit having essentially the same diameter as the diaphragm. This corresponds to letting the diaphragm sit in the bottom of a well, which provides a good shielding and mechanical protection of the diaphragm and connections and reducing the risk that the closure of a port will change the frequency response of the transducer.

A further advantageous embodiment is in particular that the port is constituted by a narrow slit. This has the particular advantage that it is difficult accidentally to cover the whole length of the slit, which reduces the risk that the port will change its properties materially during practical use. A further embodiment provides a non-wettable material for the slit surround.

An advantageous embodiment of the invention is in particular that an elastic material capable of transmitting mechanical vibration is provided in sealing relationship between the skin and the diaphragm. While the diaphragm may be made of stainless steel which is generally regarded as inert with respect to skin, there may be cases of nickel allergy, and for this reason and for normal surface protection of the diaphragm it may be desirable to provide the transducer with a layer of an elastomer. The skilled person will be able to select a material which has suitable transmission properties for this application.

A further advantageous embodiment is in particular that the acoustical network means comprises damping material.

A further advantageous embodiment is in particular that the cylindrical conduit is provided with a damping material.

A further advantageous embodiment is in particular that damping material is used as a resistive element in a port.

A further advantageous embodiment is in particular that the damping material has water-repellent qualities.

The invention will be further described with reference to the drawing, in which three transducers are described, the first (Type I) having an enclosed space in contact with the rear of the diaphragm and only in indirect contact with the surrounding air, the second (Type II) having an opening leading to the rear of the diaphragm as the most primitive case of an acoustical network directly connected to the surrounding air that will function according to the invention, and the third (Type III) having a closed volume with a port as a further but more sophisticated case of an acoustical network that will function according to the invention. Each transducer is documented by figures showing its equivalent diagram and figures showing the results obtained by simulation based on the dimensions of a useful transducer and the forces created during its practical use. Note that the absolute levels of the curves expressed in dB have no physical meaning as such, as the sound sources in the various situations have been normalised to unity. The content of the figures is as follows:

DETAILED DESCRIPTION OF THE INVENTION

In the equivalent circuits and the expressions of their properties, the following nomenclature is adhered to:

Sh: Effective application area towards tissue of inactive transducer housing (e.g. calculated from the housing radius ah and the sensor diaphragm radius ad for concentrically distributed area elements)

Zhr: Mechanical domain radiation impedance from transducer housing into the ambience calculated from Sh Zhm: Mechanical domain impedance of the transducer housing mass (Mh)

Zht: Mechanical domain tissue impedance acting on transducer housing (calculated from Sh). Consists of discrete elements Rht, Mht and Cht Zha: Mechanical impedance of hand/arm holding the transducer housing (approximately 40 Ns/m)

Sd: Effective application area towards tissue of active sensor diaphragm (calculated from the sensor diaphragm radius ad for concentrically distributed area elements)

Zhr: Mechanical domain radiation impedance from sensor diaphragm (simple rear side transducer opening of same area as diaphragm) into the ambience calculated from Sd Zdc: Mechanical domain impedance of sensor diaphragm compliance (Cd)

Zdt: Mechanical domain tissue impedance acting on sensor diaphragm (calculated from Sd). Consists of discrete elements Rdt, Mdt and Cdt Zpv: Acoustical domain impedance of air-chamber volume (Vp) compliance (behind sensor diaphragm, not including port)

Zpp: Acoustical domain impedance of port consisting of the discrete elements Rp and Mp Zpr: Mechanical domain radiation impedance from port opening into the ambience The calculations are based on the following design values of the properties of a housing with transducer according to one embodiment of the invention:

ah=20 mm
ad=6 mm
mh=50 g
cd=8 m/N
Vp=0.4ml
a=0.5 mm
b=4mm
l=15mm
F=4 N (the force of application of the transducer on the thorax)

Figure 1A:
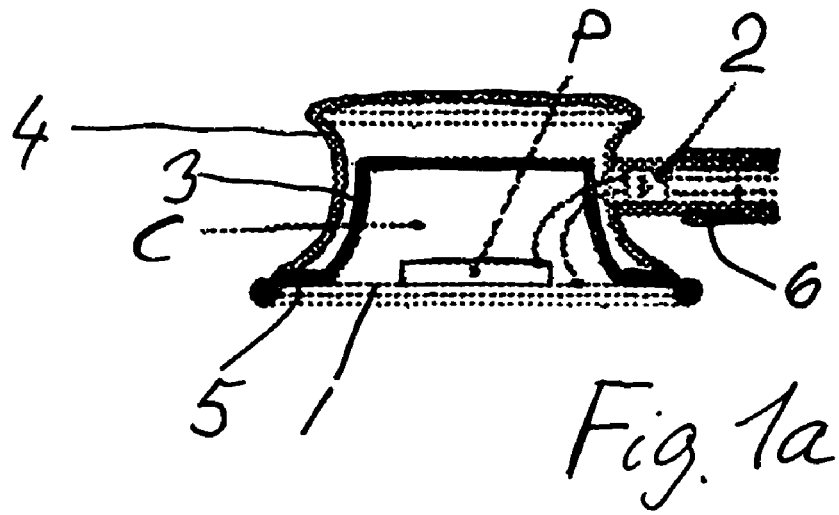
FIG. 1a shows the construction of a prior art transducer.
Figure 1:
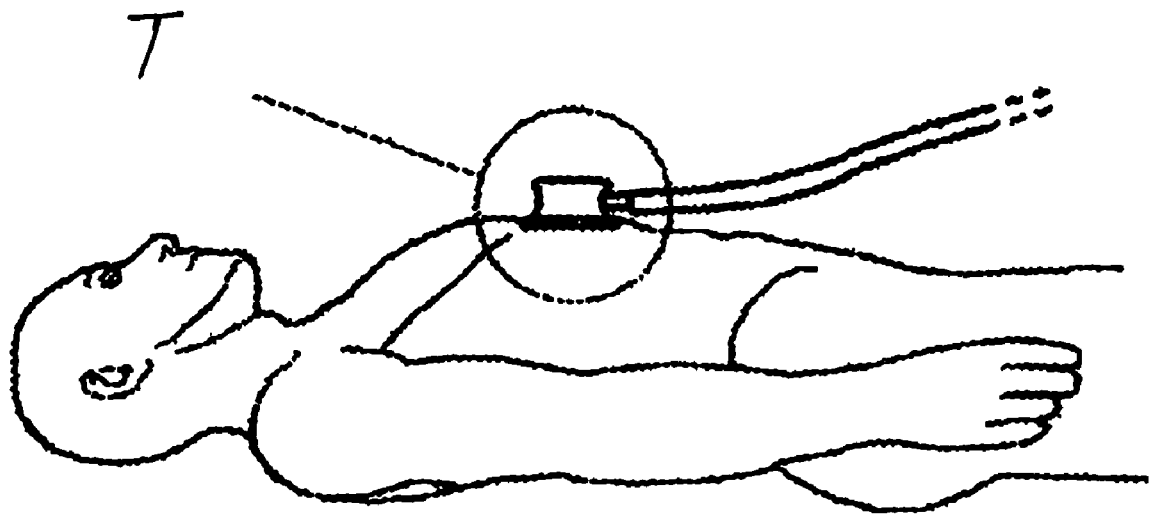
FIG. 1 shows a transducer according to prior art placed on the skin of a body.

In FIG. 1 is seen a section of a body resting on its back with a transducer T placed against the skin. The transducer shown in FIG. 1a is comprised of an outer housing 4 having an inner housing 3 holding a diaphragm 1 by its rim and creating a surround 5. Furthermore, there is a clamping arrangement 6 for the signal lead and its electrostatic shielding. The housing may also hold a pre-amplifier and impedance converter 2, e.g. using a phantom power supply. The diaphragm 1 may be a transflexural piezoelectric laminate known per se which gives off a voltage when flexed or a piezoelectric element P. One electrode consists of the actual metallic diaphragm, and the other is deposited onto the other side of the thin sheet of piezoelectric material. The diaphragm is mounted flush with or at least in the same plane as the surrounding part of the housing, and the surround 5 has a diameter or width such that airtight contact with the skin ensured. The housing is closed, thereby shielding the rear side of the diaphragm from airborne sound and creating a cavity C, which is a general representation of the prior art.

Figure 2:
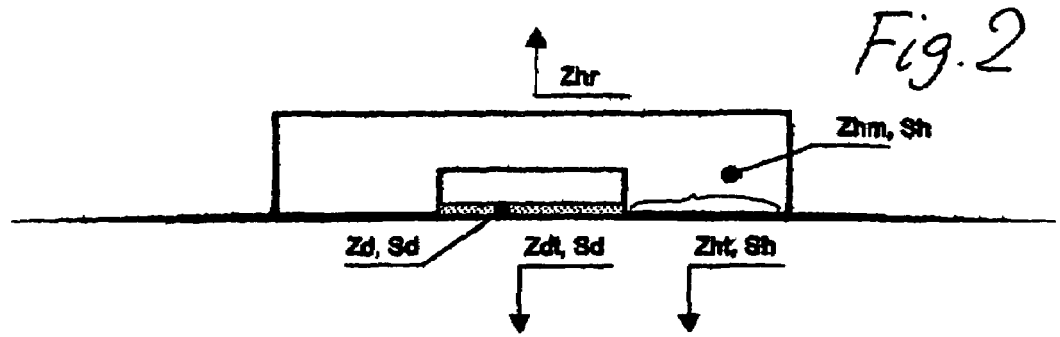
FIG. 2 identifies the components of a transducer according to a first embodiment of the invention (Type I)
Figure 3:
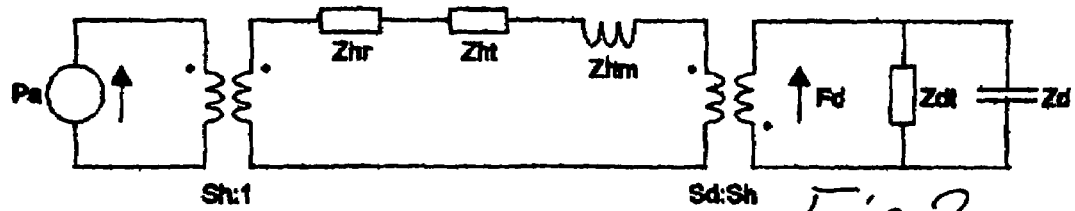
FIG. 3 shows an electrical equivalent circuit of the transducer shown in FIG. 2.

In FIG. 2 is seen a simplified layout of the components in a transducer according to the invention, and in FIG. 3 is shown the electrical equivalent circuit of the transmission path from ambient noise via the transducer housing and to the front side of the sensor diaphragm (the side in touch with the body). Ambient noise is introduced to the front side of the sensor diaphragm (facing the tissue) as the ambient noise pressure signal pushes on the transducer housing, thereby causing compression (pressure) in the underlying tissue which acts on the sensor diaphragm. A rigid mass-less piston (of surface area Sd) supported by a spring (Zd) attached to the transducer housing is a valid approximation for the fixation of the flexible sensor diaphragm onto the transducer housing.

For reasons of convenience the ambient noise picked-up can be split in two 'stages', first the ambient noise pressure signal couples to the transducer housing (via the housing radiation impedance acting as generator output impedance) where it may be transformed to a mechanical force signal and the loading from housing mass as well as attached tissue impedance (e.g., thorax impedance) may be introduced. Then this resulting input force signal undergoes an area transformation, from the inactive housing application area Sh over to the active sensor area Sd, where the loading contributions from the sensor diaphragm (primarily mechanical compliance) and its underlying tissue can be applied. FIG. 3 shows the electrical equivalent circuit of the transmission path from ambient noise via the transducer housing and to the front side of the sensor diaphragm. The sensor output is assumed proportional with the force across the sensor diaphragm compliance element. The resulting force acting on the sensor diaphragm may be calculated using (1). Note the sign inversion on the final impact due to the reaction from the tissue causing a downward force on top of the housing to act upwards on the sensor diaphragm.

$$F_{amb,closed} = -P_a Sd \frac{\left(\frac{Sh}{Sd}\right)^2 (Zd\|Zdt)}{\left(\frac{Sh}{Sd}\right)^2 (Zd\|Zdt) + Zhr + Zht + Zhm} \quad (1)$$

In the expression Pa denotes the input ambient pressure noise signal and Famb, closed denotes the resulting impact on the frontal side of the sensor diaphragm. Furthermore Zd is the sensor diaphragm mechanical impedance calculated from (2) where Cd is the diaphragm mechanical compliance $$Zd = \frac{1}{j\omega Cd} \quad (2)$$

Furthermore Zdt denotes contribution from the tissue impedance acting on the sensor diaphragm, a single degree of freedom system (SDOF mass-, compliance- and damping in series) in dependence of application force and application surface area e.g. as adapted from Vermarien H. and van Vollenhoven E.: "The recording of heart vibrations: a problem of vibration measurement on soft tissue", Medical & Biological Engineering & Computing, 1984, 22, pp 168-178. In accordance with this source the average human thorax tissue impedance associated with a circular application surface of diameter 30 mm applied under 0.6 N of force against the tissue would result in an approximate set of SDOF elements of mass Mt=5.4 gr., compliance Ct=0.62 mm/N and damping Rt=4.8 Ns/m. The total tissue impedance would add up to $$Zt = Rt + j\omega Mt + \frac{1}{j\omega Ct} [\text{Ns/m}] \quad (3)$$

The housing mass mechanical loading impedance Zhm may be calculated using (4) where Mh is the housing mass.

$$Zhm = j\omega Mh \quad (4)$$

The radiation impedance Zhr may be estimated from (5) which calculates the impedance out into a $2\pi$-space, in this equation $\alpha_h$ is the equivalent radius of a circular rigid piston of same area as the housing radiation area (e.g. Sh) and k is the wave number $$\left(k = \frac{\omega}{c}\right).$$

$$Zhr = \frac{\pi}{2}\rho c k^2 \alpha_h^4 + j\omega \frac{8}{3}\rho \alpha_h^3 \quad (5)$$

In the case of the user holding the transducer by hand the hand/arm impedance loading may be included in series connection with Zhr, Zht and Zhm working within the Sh area domain. The effect on (1) is an added Zha impedance element in the denominator, where $$Zha \approx 40 [\text{Ns/m}] \quad (6)$$

In the most practical situations the rear side of the sensor diaphragm faces an enclosed volume (room allowing for diaphragm deflection) and the inherent loading of this element will in principle also affect the sensor diaphragm deflection. However, typically, this enclosed space will act as a soft spring compared to the sensor diaphragm and hence have no practical importance and as a consequence the above equivalent circuit does not contain this element. If otherwise required a representative air-chamber volume compliance impedance element should be inserted in the model in series with Zdt.

Figure 13:
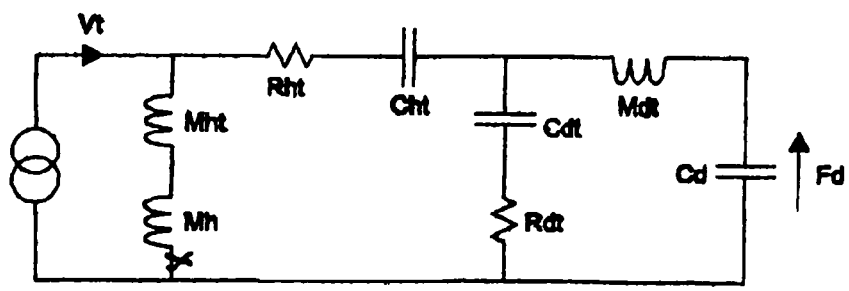
FIG. 13 shows an equivalent circuit for determining the sensitivity to the desired physiological signals.

The usefulness of a transducer for physiological signals depends to a large degree not only on its ability to suppress the influence of noise, but equally on its ability to receive the relevant physiological signals. The input to the transducer occurs via two paths, one being across the thorax impedance, the other being via the housing. The sound source itself is regarded as a high-impedance velocity sound source, and hence the electrical equivalent of the sound transmission for physiological signals may be determined according to the structure shown in FIG. 13, using the nomenclature defined above. The influence from hand/arm holding the transducer housing may be relevant in some situations, and the loading contribution from Zha may then be implemented by applying it in series with Mht and Mh as shown by the x on the drawing. Furthermore an inclusion of an enclosed air-cavity volume is implemented by adding this loading contribution in series with Cd.

The force acting on the sensor diaphragm may be calculated from the model in accordance with (7)

$$F_{phys} = V_t \frac{Zd}{Zd + Zmdt} \frac{(Zmht + Zmh)[(Zcdt + Zrdt)\|(Zmdt + Zd)]}{Zmht + Zmh + Zcht + Zrht + (Zcdt + Zrdt)\|(Zmdt + Zd)} \quad (7)$$

With expressions of the sensitivities of the transducer towards both the desired and the undesired signals being available, the performance of a transducer may usefully be expressed as the signal-to-noise (S/N) ratio, and it is frequency dependent. In order to compare examples of technical solutions or embodiments the S/N ratio will be given as a function of frequency for some typical configurations. As mentioned above, the values in dB are relative only.

Figure 4:
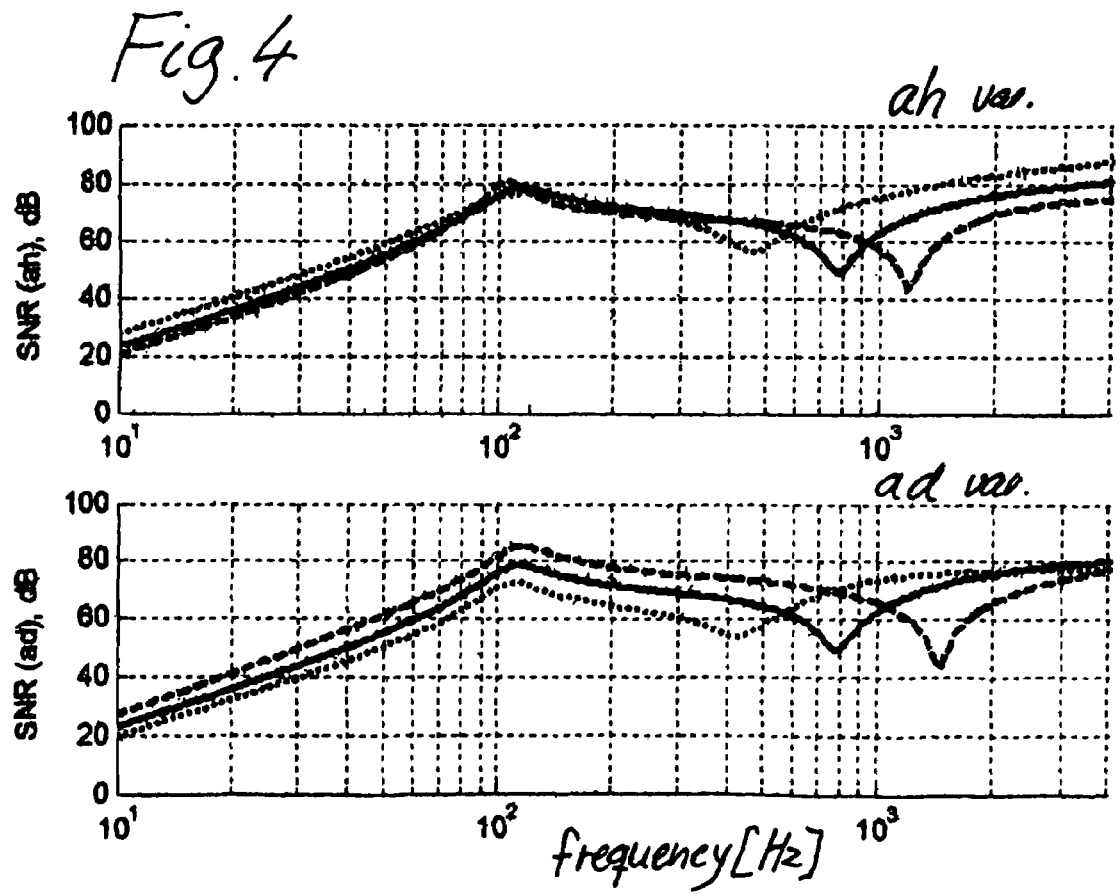
FIG. 4 shows the S/N performance of a transducer shown in FIG. 2, FIG. 5 identifies the components of a transducer according to a second embodiment of the invention (Type II)

A transducer of Type I and with the dimensions and weight given above will perform as shown in FIG. 4. Here the variation has been given in the parameters ah (top) and ad (bottom). Solid lines indicate the nominal value, the dashed lines indicate double the nominal respective values and the dotted lines indicate half the nominal respective values. From observing the results from the parameter variation it becomes clear that an increased ratio between inactive and active transducer application area improves the overall suppression of ambient noise. The result from decreasing the active area while holding the inactive fixed (ad variation) most clearly demonstrates the effect. However also for the ah-variation an increased inactive area (with fixed active sensor area) tends to move the resonant notch upward in frequency, thereby effectively expanding the operating frequency range of the transducer system. Typical auscultation sound information lies below the 1000 Hz limit and by pushing the resonance notch above this point, while maintaining a high level of suppression just beneath it, effectively improves the practical signal-to-noise ratio more, in comparison to tuning the resonance point lower and trying to compensate with even better ambient noise suppression further above the resonance point.

Due to the governing idea of the importance of the ratio between active- and inactive transducer application area (18) more than the absolute value of the physical radii of these surfaces themselves, the effective variation for the radii are defined as those causing halving, unity or doubling of the area ratio Sd/Sh from its nominal value. For the circular and concentrically distributed area elements the area ratio may be expressed as $$\frac{Sd}{Sh} = \frac{a_d^2}{a_h^2 - a_d^2} \quad (8)$$

From observing the results of the parameter analysis on the closed transducer system (FIG. 4) it becomes clear that an increased ratio between inactive and active transducer application area improves the overall suppression of ambient noise. The result from decreasing the active area while holding the inactive fixed (ad variation) most clearly demonstrates the effect. However also for the ah-variation an increased inactive area (with fixed active sensor area) tends to move the resonant notch upward in frequency, thereby effectively expanding the operating frequency range of the transducer system. Typical auscultation sound information lies below the 1000 Hz limit and by pushing the resonance notch above this point, while maintaining a high level of suppression just beneath it, effectively improves the practical signal-to-noise ratio more compared to tuning the resonance point lower and trying to compensate with even better ambient noise suppression further above the resonance point.

Figure 5:
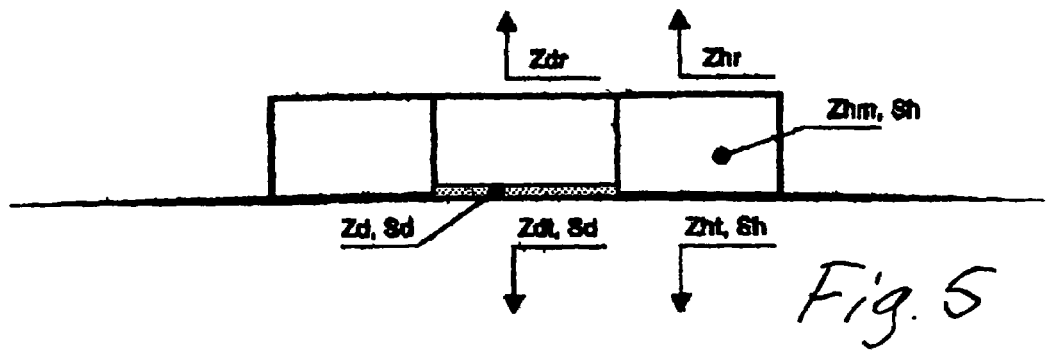

In order to reduce the susceptibility towards air-borne ambient noise of the transducer without however significantly degrading its sensitivity towards physiological vibration signals the concept of opening the transducer housing behind the sensor element has been tried (Type II), thereby allowing for counteracting ambient noise to enter the system. The simplest kind of rear side sound passage is a wide opening, causing the resulting effective pressure on the diaphragm rear side to equal that of the pressure acting on the transducer housing. FIG. 5 shows the physical layout of the simple opened transducer system with the simple opening consisting of a cylindrical conduit having essentially the same diameter as the sensor diaphragm. Thereby the ambient noise is allowed to reach the rear side of the diaphragm without any filtering action.

The effect of the simple opening on the total system ambient noise response may be calculated by the according to (9) and (10), which simply subtracts the resulting rear side force component from the complementary frontal side force component as provided above.

$$F_{d,rear,simple} = P_a Sd \quad (9)$$

$$F_{amb,simple} = \quad (10)$$
$$F_{d,closed} + F_{d,rear,simple} = P_a Sd \frac{Zhr + Zht + Zhm}{\left(\frac{Sh}{Sd}\right)^2 (Zd\|Zdt) + Zhr + Zht + Zhm}$$

An interesting detail that can be deduced from (10) is that an increased in-active transducer housing application area Sh as well as a reduced transducer housing mass seems to effectively reduce the transducer's susceptibility towards ambient noise.

Figure 6:
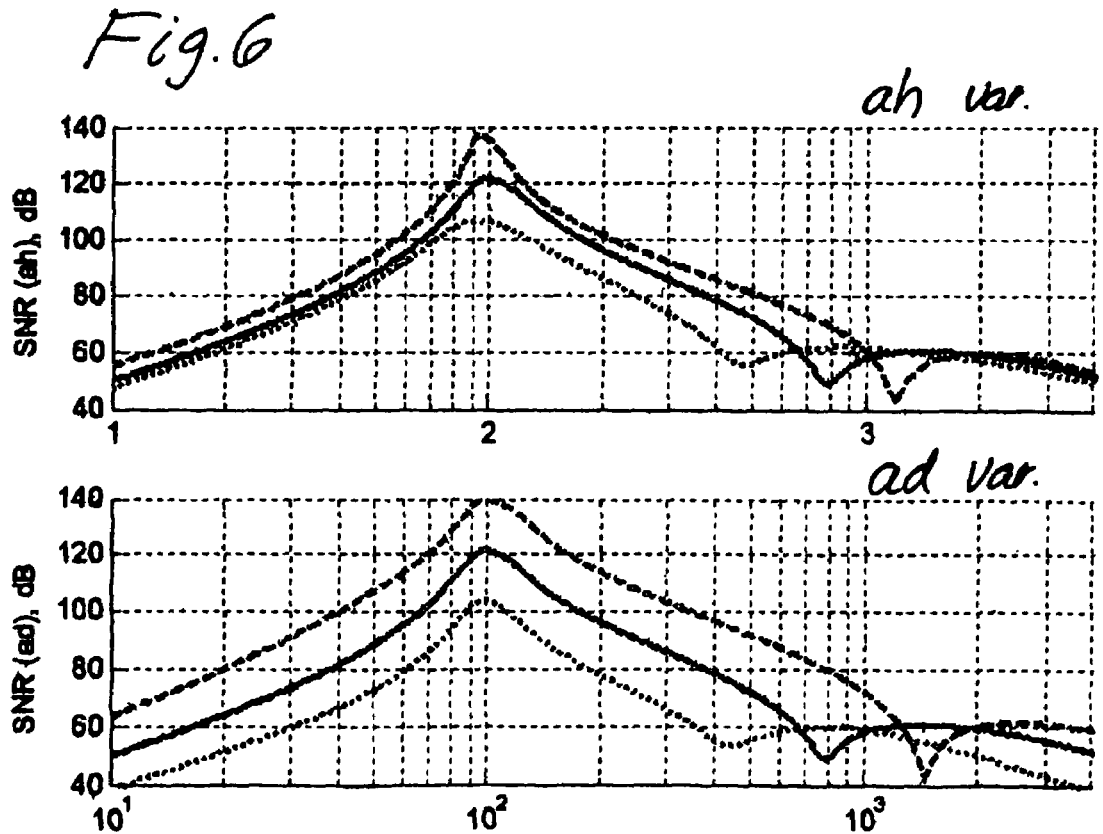
FIG. 6 shows the S/N performance of a transducer shown in FIG. 7.

A transducer of Type II and with the dimensions and weight given above will perform as shown in FIG. 6. Here the variation has been given in the parameters ah (top) and ad (bottom). Solid lines indicate the nominal value, the dashed lines indicate double the nominal respective values and the dotted lines indicate half the nominal respective values.

Inspection of the results from the simulation of the simple opened transducer system performance (FIG. 6) leaves the impression that many of the same features as stated for Type I are active in this situation as well. The fundamental difference however, of the high frequency response (at some point) always becoming inferior to that of the closed system is evident for every situation. The only way to handle this negative effect is to push the high frequency resonance notch up high as possible in the frequency range, and this feature is very convincingly dealt with by reducing the Sd/Sh area ratio. Again, the reduction of ad is identified as having the most powerful impact on the transducer performance.

This type of transducer may advantageously be provided with acoustic resistance means in the large opening connecting the rear side of the diaphragm to the surrounding air, and preferably flush with the outer surface of the housing. This acoustic resistance means will contribute to an improved S/N ratio in the relatively higher frequency range of the transducer. The means is advantageously chosen from the group comprising felt and non-woven fibrous materials and preferably provided with a water-repellent outer surface. This has the double function of providing not only a well-defined resistive part of the impedance predominantly active in the higher frequency range, but it also provides environmental protection from dust and humidity for the sensitive diaphragm. Furthermore, this type of protection will not change its acoustical properties, even when subjected to dust or water spray in limited quantities.

For both types I and II it has been demonstrated how the ratio between active and inactive application surface area Sd/Sh (more than the individual sizes of these areas seen isolated) is a central element in the optimization of the transducer system to maximal ambient noise reduction. In the nominal parameter values the area ratio had a value of ~1/10 and during the variation of the radii the value ~1/20 was tested and proven superior to the nominal value.

Figure 11:
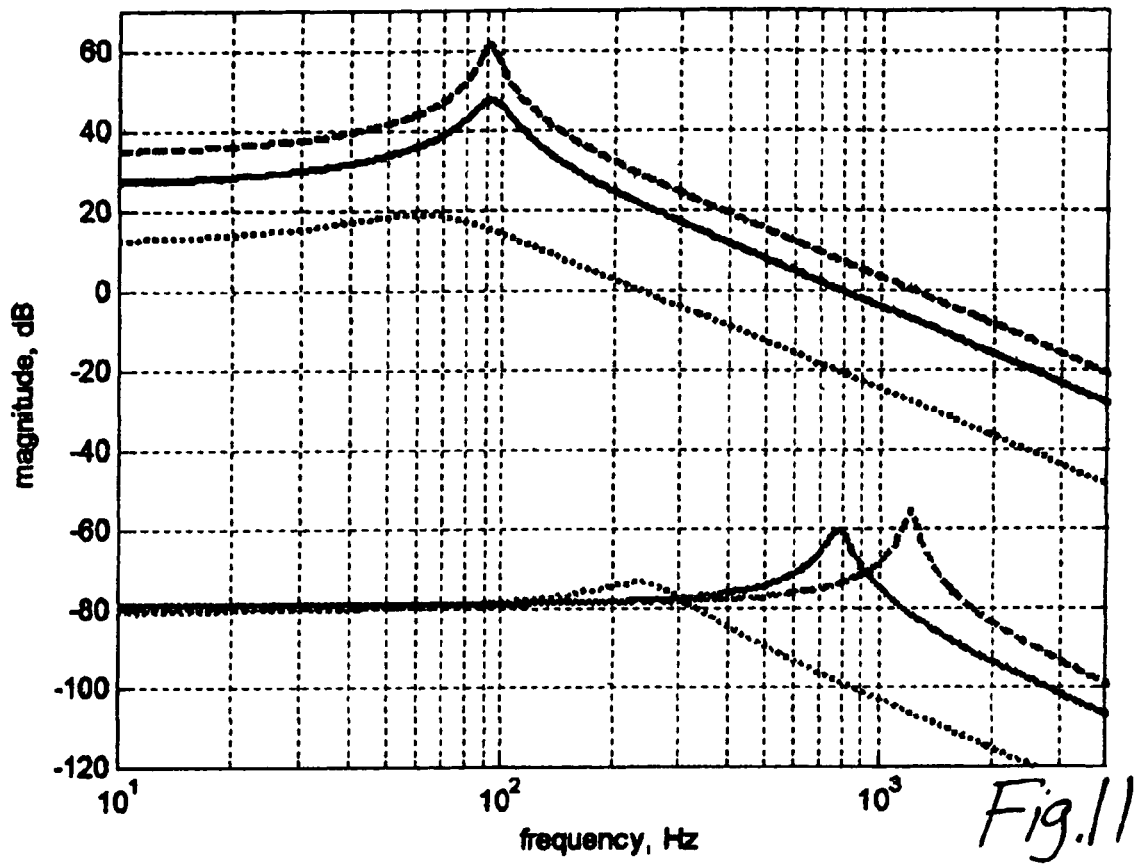
FIG. 11 shows results of changes of area ratio according to one aspect of the invention, changing the area of the housing.
Figure 12:
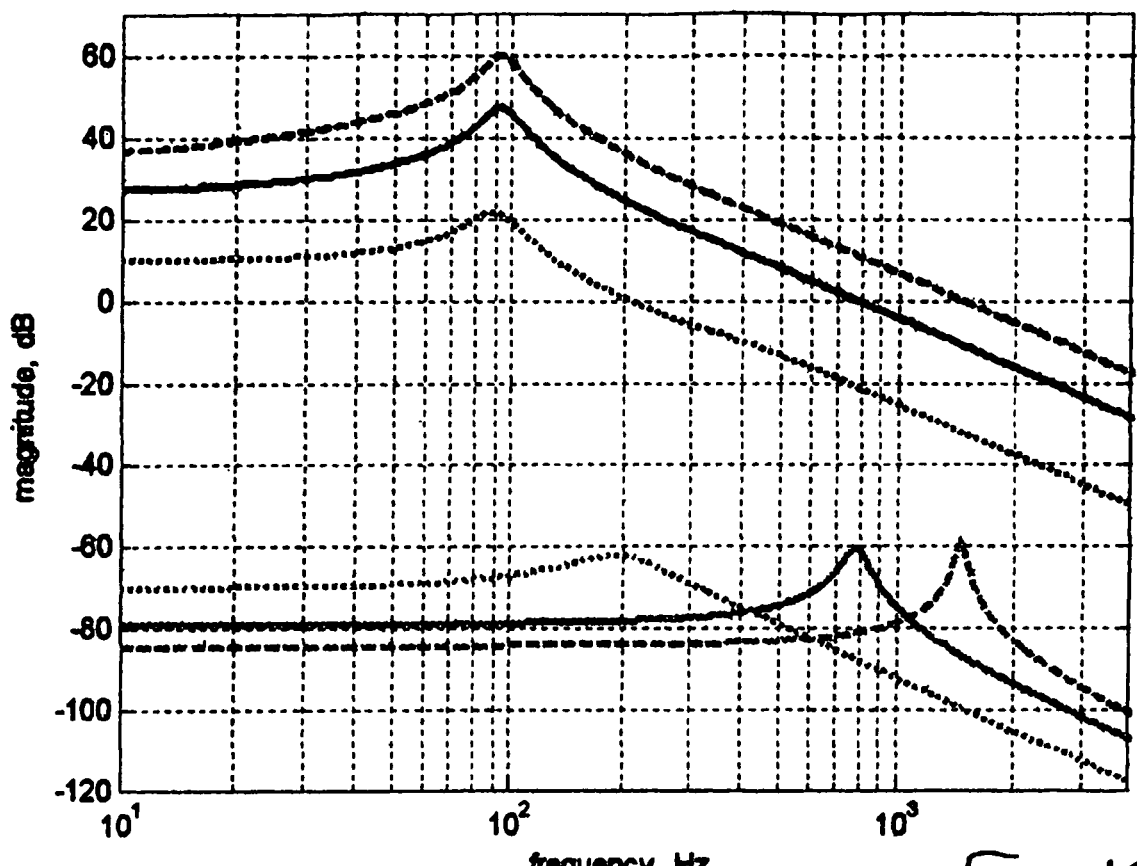
FIG. 12 shows results of changes of area ratio according to one aspect of the invention, changing the area of the diaphragm.

FIGS. 11 and 12 show simulations for the area ratio values 1/20, 1/10 and ½, realized either through ah variation (FIG. 11) or ad variation (FIG. 12). Each graph shows the noise performance for the closed system and furthermore the improvement of the simple opened system over the closed system. The lower set of curves represents the closed transducer system (Type I) response and upper set of curves show the improvement of the simple opened system (Type II) over the closed system. Area ratio Sd/Sh values of 1/20 (dashed), 1/10 (solid) and 1/2 (dotted) have been shown.

The closed system response changes dramatically under the influence of the area ratio alteration, both in overall level as well as the position of its resonance changes from ~1200 Hz (with Sd/Sh=1/20) down to ~200 Hz (with Sd/Sh=1/2). Looking at the relative performance of the simple opened system it is seen, that above the closed system response resonance the simple opened system is inferior to the closed. For the simple opened system the area ratio Sd/Sh=1/2 defines a lower limit of beneficial value of the rear side in-coupling to be located at approx. 200 Hz (for these defined physical conditions).

Considering the frequency range up to the above 200 Hz in isolation this is of cause a valid improvement in that specific frequency range, and it would possibly be satisfactory if the interest solely covered e.g. fundamental heart sounds and low frequency murmurs. To be used in a more general auscultation system (stethoscopes etc.) the 200 Hz limit is not satisfactory at all, as most hard-to-hear heart murmurs (as well as delicate lung sounds) all reside in the frequency range above 200 Hz. In the other end of the scale the Sd/Sh=1/20 performs very well indeed as it effectively moves the closed system resonance above 1000 Hz, thereby allowing for good damping in a very wide operating frequency range.

Figure 7:
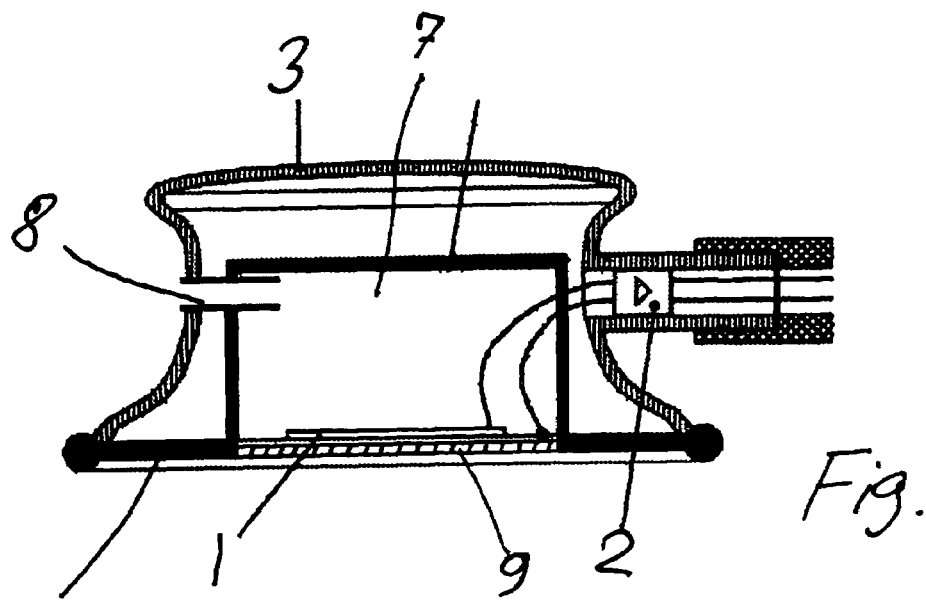
FIG. 7 shows the construction of a transducer according to a third embodiment of the invention (Type III), FIG. 8 identifies the components of the transducer shown in FIG. 7.
Figure 9:
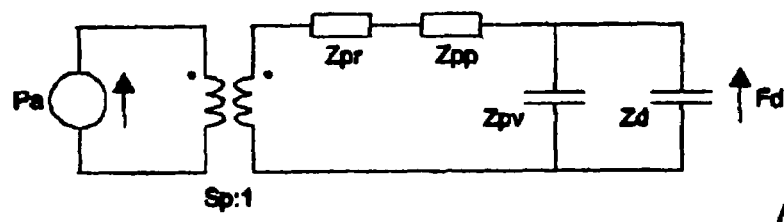
FIG. 9 shows an electrical equivalent circuit of the transducer shown i FIG. 7.

FIG. 9 shows the physical layout of a transducer system (Type III) having a combined port (an acoustical vent having a resistance and a mass element) and air-cavity volume performing a second order low-pass filtering of the ambient noise before it meets the sensor diaphragm rear side. FIG. 7 shows a Type III transducer in greater detail fitted in a housing. The cavity 7 is in communication with the surrounding air by means of a port 8 with well-defined properties. The surface of the diaphragm touching the skin may be protected by a coat or layer of material 9 that will not influence the pickup by the diaphragm, i.e. it should posses properties similar to the tissue that the diaphragm is touching. This is indicated by the hatching of the slight depression formed in the surround 5 in which the diaphragm is placed. It will be seen in the figure that the radius ad of the diaphragm is ca. 50% of the radius ah of the housing, corresponding to an area proportion of ca. 25%.

Figure 8:
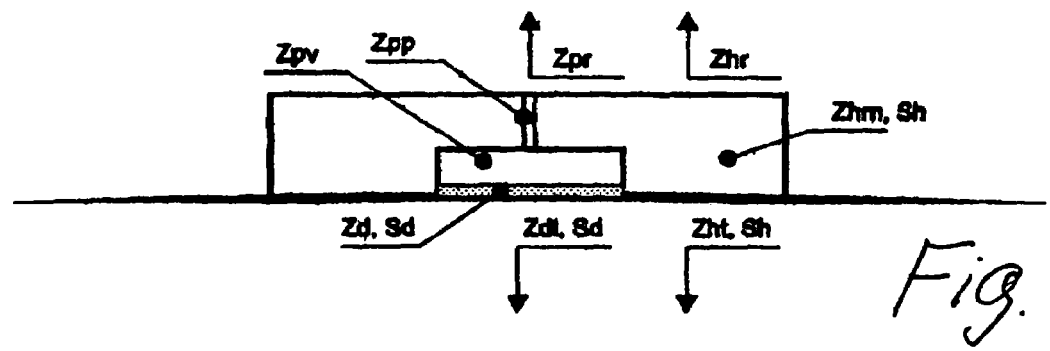

The port/volume system is characteristic in its resonance frequency and its overshoot at resonance, below resonance the system is to be considered approximately as a simple opening whereas the response above resonance is a second order low-pass roll-off. In order to accurately estimate the response, the contribution from the sensor diaphragm compliance possibly needs to be included in the modeling. The diaphragm compliance will act in parallel with the air-cavity volume compliance and in cases where the volume compliance is not significantly larger the diaphragm compliance will induce a reduced resonance frequency for the complete system. The equivalent circuit is shown in FIG. 8, which essentially shows the transmission path from the ambient noise floor to the rear side of the sensor diaphragm.

From the model the contribution from the rear side ambient noise pressure signal input may be calculated using (11)

$$F_{d,rear,port} = P_a Sd \frac{\left(\frac{Zd}{Sd^2}\right)\|Zpv}{\left(\frac{Zd}{Sd^2}\right)\|Zpv + Zpp + Zpr} \quad (11)$$

Impedance element Zpv is the air-volume acoustic compliance calculated from (13) with V denoting the cavity volume $$Zpv = \frac{\rho c^2}{j\omega V} \quad (12)$$

Furthermore, Zpp is the port acoustic impedance, consisting of a damping element and a mass element in series connection, e.g. calculated for a narrow slit which typically is introduced for purposes of elevated damping rates (14). The narrow slit impedance may be estimated from its length l (parallel to the sound propagation direction), its width a (orthogonal to sound propagation and the least distance between two opposite planes in the slit) and the slit height b the constant η denotes the air viscosity (approximately 18.3 $10^{-6}$ Ns/m).

$$Zpp = \frac{12\eta l}{a^3 b} + j\omega \frac{6}{5}\frac{\rho l}{ab} \quad (13)$$

The resulting force acting on the sensor diaphragm in system where the rear side diaphragm pressure signal has passed the port-volume acoustical filter system then becomes the sum of the contribution from each side.

$$F_{amb,port} = F_{d,closed} + F_{d,rear,port} \quad (14)$$

Figure 10:
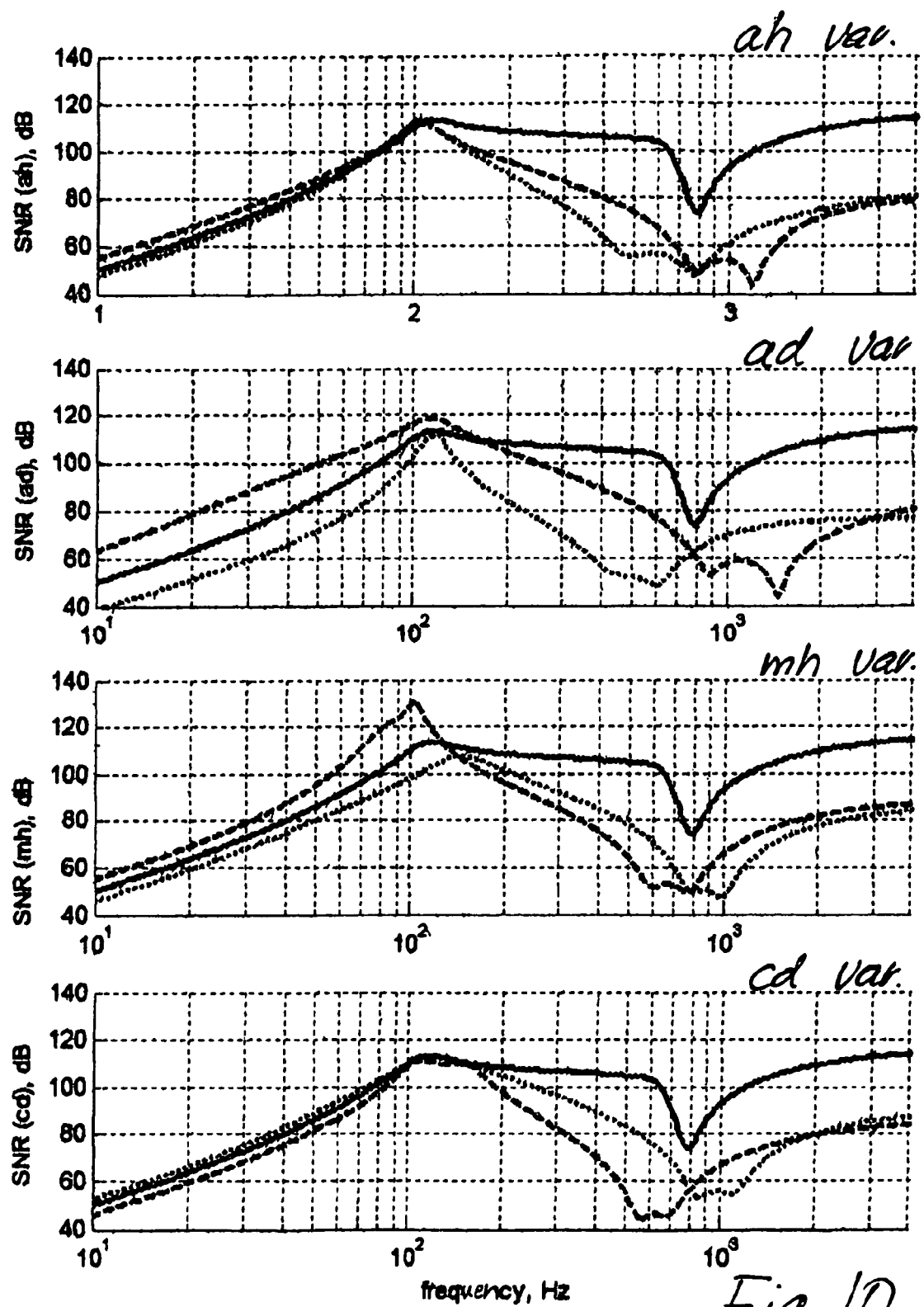
FIG. 10 shows the S/N ratio performance of the Type III transducer.

A transducer of Type III and with the dimensions and weight given above will perform as shown in FIG. 10. Here the variation has been given (top to bottom) in ah, ad, mh, and cd, the latter being the compliance of the diaphragm. Solid lines indicate the nominal value, the dashed lines indicate double the nominal respective values and the dotted lines indicate half the nominal respective values.

Besides the simple rear side opening and the port-volume filter opening described above, there exist a wide variety of interesting principles for guiding/filtering the ambient noise signal in its attack on the diaphragm rear side. Examples could include an acoustic horn, e.g. having the larger area end pointing against the surroundings and the narrow area end connecting to the sensor diaphragm. Also an acoustic waveguide consisting of multiple coupled ports and cavities, or alternatively passive diaphragms (as known from slave bass loudspeaker systems) could prove interesting in the optimization of the transducer immunity towards ambient noise.

As mentioned above, regarding type II, the acoustic resistance means may usefully be found in the group comprising felt and non-woven fibrous materials, however, they may have to be very compact. Alternatively, the port in the case of Type III, when formed as a slit in the housing, may have an appreciable length and a correspondingly narrow width. This has the particular advantage that accidental partial closure will not disturb the function to an appreciable degree. The provision of a non-wettable surface in the slit precludes any trapping of water. In practice, this may be obtained by a PTFE insert with a laser-cut slit.

Similar considerations to those mentioned above concerning Type I and Type II will conclude that also for Type III there may be obtained a distinct advantage by keeping the Sd/Sh range within the limits according to the invention, and the fact that more paramaters are available for variation in Type III enable the contribution of the Sd/Sh to be tailored to a specific desired frequency response expressed as a S/N ratio. The value 1/20 functions well in this environment.

The foregoing description of the specific embodiments will so fully reveal the general nature of the present invention that others skilled in the art can, by applying current knowledge, readily modify or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of forms without departing from the invention.

Thus, the expressions "means to . . . " and "means for . . . ", or any method step language, as may be found in the specification above and/or in the claims below, followed by a functional statement, are intended to define and cover whatever structural, physical, chemical, or electrical element or structure, or whatever method step, which may now or in the future exist which carries out the recited functions, whether or not precisely equivalent to the embodiment or embodiments disclosed in the specification above, i.e., other means or steps for carrying out the same function can be used; and it is intended that such expressions be given their broadest interpretation.

The invention claimed is:

1. A transducer assembly for transducing bioacoustic signals, comprising:
   a transducer element having a front side and a rear side;
   a housing, the housing subject to ambient noise and comprising a surface surrounding the front side of the transducer element, the transducer element and the surrounding surface of the housing situated to establish intimate coupling with a surface of a body part during use, the body part surface defining a source of the bioacoustic signals; and communicating an ambient noise through an opening in the housing and to the rear side of the transducer element and receiving ambient noise at the front side of the transducer element when the housing establishes intimate coupling with the body part surface during use; and thereby reducing ambient noise and
   an ambient noise suppression arrangement comprising a selected area ratio of an effective area of the transducer element sd relative to an area of the surrounding surface of the housing sh, wherein the effective area of the transducer element sd is less than 50% of the surrounding surface area sh and the selected area ratio provides for increased ambient noise suppression within a frequency range associated with the bioacoustic signals.

2. The transducer assembly of claim 1, wherein the selected area ratio is defined by $0.50 \geq sd/sh \geq 0.001$.

3. The transducer assembly of claim 1, wherein the selected area ratio is defined by $0.20 \geq sd/sh \geq 0.05$.

4. The transducer assembly of claim 1, wherein the selected area ratio provides for an increased signal-to-noise ratio (SNR) defined by a ratio of bioacoustic signal strength relative to ambient noise strength, wherein the increased SNR is achieved by a decrease in the net ambient noise strength.

5. The transducer assembly of claim 1, wherein the ambient noise suppression arrangement comprises an acoustical network through which ambient noise is communicated from air surrounding the housing to the rear side of the transducer element, the acoustical network configured to increase ambient noise suppression within the frequency range associated with the bioacoustic signals.

6. The transducer assembly of claim 1, further comprising interfacing material disposed over at least the front side of the transducer element and configured to provide good acoustical coupling between the transducer element and the surface of the body part during use.

7. A transducer assembly for transducing bioacoustic signals, comprising:
   a skin coupling surface comprising a transducer element and having a front side and a rear side;
   a housing, the housing subject to ambient airborne noise and comprising a surface surrounding the front side of the transducer element, the transducer element and the surrounding surface of the housing situated to establish intimate coupling with a surface of a body part during use, the body part surface defining a source of the bioacoustic signals; and
   an ambient noise suppression arrangement configured to suppress ambient airborne noise coupled to the rear side of the skin coupling surface and ambient airborne noise coupled to an opening of the housing and the front side of the skin coupling surface, the ambient noise suppression arrangement configured to upwardly shift a transducer assembly resonance notch beyond an upper frequency limit of a frequency range associated with particular bioacoustic signals wherein the ambient noise suppression arrangement comprises a selected area ratio of an effective area of the transducer element relative to an area of the surrounding surface of the housing.

8. The transducer assembly of claim 7, wherein the effective area of the transducer element is less than 50% of the surrounding surface area and the selected area ratio provides for increased ambient noise suppression within a frequency range associated with the particular bioacoustic signals.

9. A method of transducing bioacoustic signals, comprising:

providing a transducer assembly comprising a housing and a transducer element having a front side and a rear side, the housing comprising a surface surrounding the front side of the transducer element, the transducer element and the surrounding surface of the housing situated to establish intimate coupling with a surface of a body part during use, the body part surface defining a source of the bioacoustic signals;

communicating ambient noise through an opening in the housing and to the back side of the transducer element;

receiving ambient noise at the front side of the transducer element when the housing establishes intimate coupling with the body part surface during use; and reducing ambient noise influencing the transducer element by upwardly shifting a transducer assembly resonance notch beyond an upper frequency limit of a frequency range associated with particular bioacoustic signals;

wherein reducing ambient noise influencing the transducer element comprises providing a selected area ratio of an effective area of the transducer element relative to an area of the surrounding surface of the housing, wherein the effective area of the transducer element is less than 50% of the surrounding surface area.

10. The method of claim 9, wherein communicating ambient noise through the housing opening comprises communicating the ambient noise through an acoustical network.

11. The method of claim 9, wherein the upper frequency limit is a frequency greater than 1000 Hz.

12. The method of claim 9, wherein the upper frequency limit is a frequency less than 1000 Hz.

* * * * *